United States Patent
Kim et al.

(10) Patent No.: US 6,720,023 B1
(45) Date of Patent: Apr. 13, 2004

(54) METHOD FOR PREPARATION OF THE SUPERSATURATED SOLUTION OF CALCIUM PHOSPHATE AND THE THIN FILM OF CALCIUM PHOSPHATE CRYSTAL BY USING THE SOLUTION

(75) Inventors: Hyun-Man Kim, #506-205 Zookong Apt., Chamsil 5-dong, Songpa-ku, Seoul 138-225 (KR); Jea-Seung Ko, Seoul (KR); Yoon-Ji Kim, Seoul (KR); Soo-Jin Park, Seoul (KR)

(73) Assignees: Hyun-Man Kim, Seoul (KR); Oscotec Inc., Choongcheongnam-do (KR)

( * ) Notice: Subject to any disclaimer, the term of this patent is extended or adjusted under 35 U.S.C. 154(b) by 0 days.

(21) Appl. No.: 09/786,552

(22) PCT Filed: Sep. 15, 1999

(86) PCT No.: PCT/KR99/00552

§ 371 (c)(1),
(2), (4) Date: Mar. 2, 2001

(87) PCT Pub. No.: WO00/15018

PCT Pub. Date: Mar. 23, 2000

(30) Foreign Application Priority Data

Sep. 17, 1998 (KR) .............................. 98-38553
Sep. 10, 1999 (KR) ......................... 1999-38528

(51) Int. Cl.$^7$ .............................................. C01B 25/32
(52) U.S. Cl. ...................... 427/2.27; 423/308; 423/309; 423/311
(58) Field of Search ................................. 423/308, 309, 423/311; 427/2.27

(56) References Cited

U.S. PATENT DOCUMENTS

| 4,349,518 A | * | 9/1982 | Long et al. ................ 423/308 |
| 4,366,183 A | * | 12/1982 | Ghommidh et al. ........ 427/2.27 |
| 4,849,193 A | * | 7/1989 | Palmer et al. ............... 423/308 |
| 4,891,198 A | * | 1/1990 | Ackilli et al. ................ 423/308 |
| 5,068,122 A | * | 11/1991 | Kokubo et al. ............. 427/2.27 |
| 5,077,079 A | * | 12/1991 | Kawamura et al. ........ 427/2.27 |

(List continued on next page.)

OTHER PUBLICATIONS

WO 97/37932, Oct. 16, 1997.*
An article entitled "Composition and structure of the apatite formed on PET substrates in SBF modified with various ioinic activity products", By Kim et al., published John Wiley & Sons, Inc. Jan., 1999, pp. 228–235.
An article entitled, "Critical ageing of hydroxyapatite sol–gel solutions", By Chai et al., published by Elsevier Science Ltd., May, 1998, pp. 2291–2296.
An article entitled, "Physical, chemical, and biological characterization of pulsed laser deposited and plasma sputtered hydroxyapatite thin films on titanium alloy", By Lo et al., published by John Wiley & Sons Inc. Oct. 1999, pp. 536–545.

(List continued on next page.)

Primary Examiner—Wayne A. Langel
(74) Attorney, Agent, or Firm—Bachman & LaPointe, P.C.

(57) ABSTRACT

The present invention relates to a method for preparation of the supersaturated calcium and phosphate ions solution and a method for preparation of the thin film of calcium phosphate crystal on solid surface by using the said solution. Particularly, the lowered temperature and/or the use of suitable buffer system inhibit the nucleation of calcium phosphate in aqueous solution, and thereby highly supersaturated calcium and phosphate ions solution can be prepared. And the thin film of calcium phosphate crystal on solid surface can be prepared with rapidity and good quality of high reactivity and low crystallinity by using the said solution. Also the thin film of calcium phosphate crystal prepared according to the present invention has biocompatibility and can be applied as biomaterials.

11 Claims, 1 Drawing Sheet

U.S. PATENT DOCUMENTS 5,458,863 A * 10/1995 Klassen ...................... 423/308
5,730,598 A * 3/1998 Story et al. ................ 427/2.27
5,766,669 A * 6/1998 Pugh et al. ................ 427/2.27
5,783,217 A * 7/1998 Lee et al. ................... 423/308
6,110,851 A * 8/2000 Wiedemann ................ 423/308
6,129,928 A * 10/2000 Sarangapani et al. ...... 427/2.27

OTHER PUBLICATIONS

An article entitled, "Apatite layer–coating titanium for use as bone bonding implants", By Yan et al., published by Elsevier Science Limited, Biomaterials, 1997 vol. 18, No. 17, pp. 1185–1190, (no month).

* cited by examiner

METHOD FOR PREPARATION OF THE SUPERSATURATED SOLUTION OF CALCIUM PHOSPHATE AND THE THIN FILM OF CALCIUM PHOSPHATE CRYSTAL BY USING THE SOLUTION

BACKGROUND OF THE INVENTION

The present invention relates to a method for preparation of the supersaturated calcium and phosphate ions solution and a method for preparation of the thin film of calcium phosphate crystal on solid surface by using the said solution. Particularly, the lowered temperature and/or the use of suitable buffer system inhibit the nucleation of calcium phosphate in aqueous solution, and thereby highly supersaturated calcium and phosphate ions solution can be prepared. And the thin film of calcium phosphate crystal on solid surface can be prepared with rapidity and good quality of high reactivity and low crystallinity by using the said solution.

Calcium phosphate crystal has been known to have biocompatibility. The apatite crystal is the only type of calcium phosphate crystals in calcified tissues (H.-M. Kim et al., *J. Bone Miner. Res.* 10, 1589–1601 (1995); U.S. Pat. No. 5,565,502; and U.S. Pat. No. 5,691,397), and it has been used as substitute for bone. Also it has been widely used for enhancing the biocompatibility to tissues by forming the apatite layer on biomaterial surface of metals or as solid particles (R. G. T. Geesink, *Clin. Orthop. Relat. Res.* 261, 39–58 (1990); and M. G. Dunn and S. H. Maxian, *J. Long Term Effect. Med. Implants*, 1, 193–203 (1991)).

So far, in order to enhance the biocompatibility by using calcium phosphate crystal, various coating methods have been developed for forming calcium phosphate crystal, especially apatite layer on the surface of substrate such as titanium, etc. The plasma coating has been most widely used. With the plasma coating, the apatite layer is formed and grown at high temperature, therefore it comprises hydroxy apatite which has low bioreactivity due to high crystallinity and large size. Also it has been known that the byproducts such as other phases of calcium phosphate or calcium oxide are formed in addition to the apatite crystal (H.-G. Pfaff et al., Properties of HA-Coatings in "*Bioceramics*", vol. 6, eds., P. Ducheyne and D. Christiansen, pp. 419–424, Butterworth-Heinemann Ltd. (1993)). It has to be confirmed clearly what negative effect the said byproduct has on biocompatibility. Thus, there has been a demand to develop a method to form apatite crystal layer with properties similar to those of bone apatite crystal, i.e. having favorable bio-reactivity due to low crystallinity and wide reactive surface area due to small size, on substrate surface.

Pure hydroxy apatite crystals consisting of calcium, phosphate and hydroxyl ions are stoichiometric crystals of rods with high crystallinity while biocrystals isolated form bone or calcified cartilage are nonstoichiometric apatites of low crystallinity (Elliott J. C. *In Structure and Chemistry of the Apatites and Other Calcium Orthophosphates, Studies in Inorganic Chemistry* 18, Amsterdam: Elsevier, pp 111–190 (1994)). Biocrystals are thin plates of extremely small nanocrystals (27.3×15.8 nm for bone, 103×68 nm for calcified cartilage; length×width) of extensive specific surface that makes them metabolically active with high surface reactivity (H.-M. Kim et. al., *J. Bone Miner. Res.* 10:1589–1601 (1995), Posner A. S. et. al. *Skeletal Research: An Experimental Approach*, Academic Press: New York, pp 167–192 (1979)).

In order to form a crystal layer of which crystallographic properties mimic those of brocrystals, a method to form the crystal layer directly on solid surface at low temperature has been developed by using the solution of calcium and phosphate ions. However, the concentration of ions cannot be kept high because of spontaneous nucleation in supersaturated solution and it was difficult to keep the concentration product $[Ca^{2+}] \times [HPO_4^{2-}]$ of the solution above 6 mM$^2$ (H. B. Wen et al., *J. Biomed. Mater. Res.* 41, 227–236 (1998)). In addition, in such low supersaturated concentration, its application to formation of crystal layer on solid surface was very limited to narrow conditions of temperature and solid surfaces. That is, the temperature had to be kept at about 37° C., and the coating procedures needed long time, over one month depending on the condition of surface. Temperature controls the crystallographic nature of the crystal layer. In addition, much lowered temperature is needed to attach the temperature-sensitive and bioactive materials with the crystal on the surface. Therefore, in case that the temperature has to be controlled or lowered, the said method can not be employed. And only the charged surface can be employed for the substrate in most of cases.

We, the inventors of the present invention, have developed a method for preparation of the supersaturated calcium and phosphate ions solution and a method for preparation of the thin film of calcium phosphate crystal on solid surface by using the said solution. Particularly, the lowered temperature and/or the use of suitable buffer system inhibited the nucleation of calcium phosphate in aqueous solution, and thereby highly supersaturated calcium and phosphate ions solution could be prepared. And the thin film of calcium phosphate crystal on solid surface could be prepared with rapidity and good quality of high reactivity and low crystallinity by using the said solution. Also the thin film of calcium phosphate crystal prepared according to the present invention has biocompatibility.

SUMMARY OF THE INVENTION

The object of the present invention is to provide a method for preparation of the supersaturated solution of calcium phosphate keeping the concentration of calcium and phosphate ions high.

The another object of the present invention is to provide a method for preparation of the thin film of calcium phosphate crystal on solid surface using the said solution with rapidity and good quality of high reactivity and low crystallinity.

DETAILED DESCRIPTION OF THE INVENTION

Figure 1:
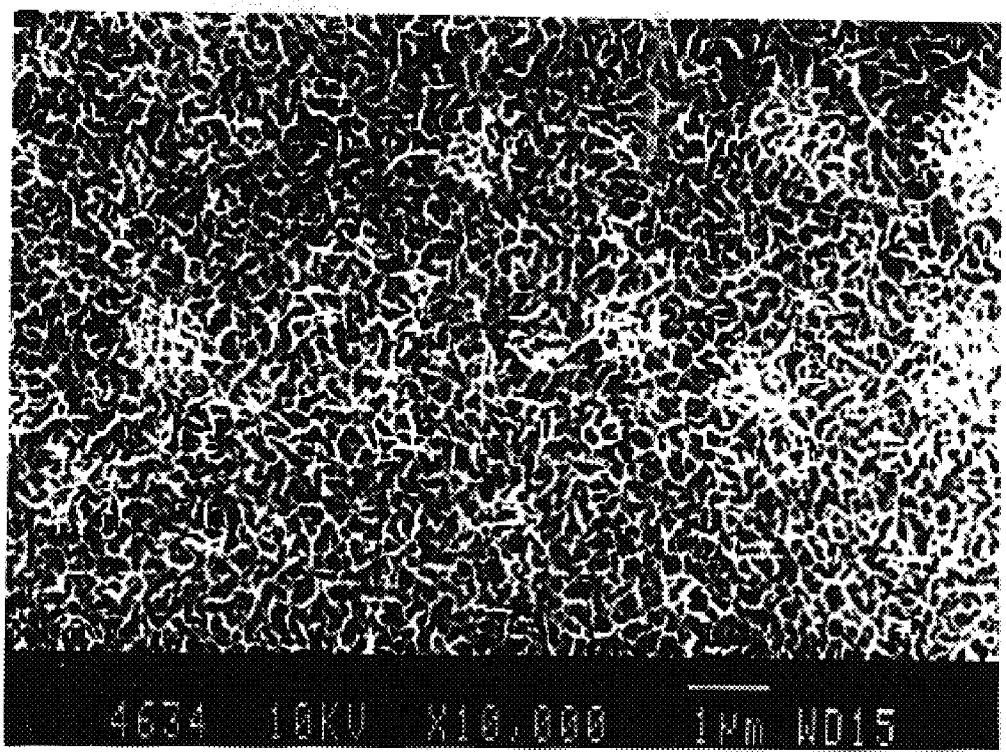
FIG. 1 is the SEM image (X10,000) of the thin film of apatite crystals.

The present invention provides a method for preparation of supersaturated solution of calcium phosphate keeping the concentration of calcium and phosphate ions high, comprising the steps of:

1) preparing a highly concentrated solution of calcium and phosphate ions by dissolving calcium phosphate crystals or salts of calcium and of phosphate in acidic solution (step 1);

2) mixing the acidic solution of highly concentrated calcium and phosphate ions of the step 1 with alkaline solution at low temperature (step 2); and 3) excluding amorphous calcium phosphate particles or crystals which can act as nuclei for nucleation and growth of crystals, from the solution prepared in step 2, to inhibit further nucleation reaction and growth of crystals in solution (step 3).

In step 2, the low temperature inhibits homogeneous nucleation of calcium phosphate in solution and thereby free ions are saved for preparation of thin film of calcium phosphate later. And the inhibition effect is more enhanced by using suitable buffer system.

Any salts of calcium and of phosphate can be employed in the present invention. And any calcium phosphate crystal can be employed in the present invention. Calcium phosphate crystal used in the present invention can be prepared by the known synthetic method. For example, as reported by C. Rey et al. [*Calcif. Tissue Int.* 45, 157–164 (1989); and *Calcif. Tissue Int.* 46, 157–164 (1990)], a solution of $Ca(NO_3)_2 \cdot 4H_2O$ dissolved in distilled water and a solution of $(NH_4)_2HPO_4$ and liq. ammonia dissolved in distilled water are rapidly mixed, filtered and freeze-dried to prepare apatite. Also $CaCl_2 \cdot 2H_2O$ and $KH_2PO_4$ can be employed. Apatite crystal used in the present invention is also obtained by separating it from bone (H.-M. Kim et al. *J. Bone Miner. Res.* 10, 1589–1601 (1995)). In case of using synthetic calcium phosphate crystal, there is advantage that the type of ions contained in the solution can be limited only to ions comprising the crystal such as calcium ion, phosphate ion, carbonate ion, etc. And the solution prepared by decalcifying calcified tissues with acidic solution can be used in step 2.

Any acid can be employed for the acidic solution used for dissolving the above calcium phosphate crystal. For example, general organic acids such as N-[2-hydroxyethyl]piperazine-N'-[2-ethanesulfonic acid], N-tris-[hydroxymethyl]methyl-2-aminoethanesulfonic acid, 1,4-piperazinediethanesulfonic acid, (3-N-morpholino)propanesulfonic acid and $CH_3COOH$, inorganic acids such as HCl, HBr, HI, $H_2SO_4$, $H_3PO_4$, $HNO_3$, and $H_2CO_3$, or their mixture can be employed for the acidic solution. Preferably HCl and N-[2-hydroxyethyl]piperazine-N'-[2-ethanesulfonic acid] are used. The calcium phosphate crystal is then dissolved over the concentration at which it is possible to form crystal precipitate, in mixture with alkaline solution.

The alkaline solution is added to an acidic solution wherein calcium phosphate is dissolved, to precipitate amorphous calcium phosphate particle. At this time the temperature of the two solutions and the reaction temperature should be kept low in order to inhibit nucleation of calcium phosphate in solution for saving free ions. Preferably, the temperature is maintained at 0–37° C.

As an alkaline solution, general inorganic bases such as NaOH, KOH, LiOH, Ca(OH), Mg(OH), and NHOH, organic bases selected from the group consisting of tris [hydroxymethyl]amino methane, bis[2-hydroxyethyl] aminotris[hydroxymethyl]methane and 1,3-bis [tris (hydroxymethyl)methylamino]propane, etc. or their mixture can be employed. The organic buffer is selected depending on the preferred pH, considering the buffering range of each buffer. And the critical temperature at which it is possible to prepare a supersaturated calcium phosphate ion solution, may be higher in case of using an organic buffer than in case of using an inorganic base.

The pH of the mixture solution is set to be 6.0–8.0 by adding the alkaline solution, preferably, 7.0–7.6. The crystallographic nature of calcium phosphate crystal depends on pH. Therefore the desired type of crystal can be obtained by controlling pH. The pH's of supersaturated solution for obtaining dicalcium phosphate dihydrate crystal, octacalcium phosphate crystal and apatite crystal film widely used as biomaterials are 6.0–6.5, 6.5–6.8 and 6.8–8.0, respectively.

Then, in order to obtain apatite film having uniform surface by using the said solution, it is preferable to remove the amorphous calcium phosphate particles produced in the solution. The amorphous calcium phosphate particles are excluded from the solution neutralized with alkaline solution by conventional filtration or centrifugation. In case of filtration microbes can be excluded simultaneously, therefore there is no need of further sterilization.

The ion concentration product of supersaturated solution of calcium phosphate prepared according to the present invention is 6.0–30.0 $mM^2$ $[Ca^{2+}] \times [HPO_4^{2-}]$ depending on the reaction condition. The formation of precipitate or crystal in this solution is suppressed owing to low temperature during the said process although the ion concentration is high enough to form precipitate by homogenous nucleation. However, when the solution is in contact with solid surface, the crystal can be formed, attached and grown on the surface by heterogeneous nucleation beyond the inhibition effect of nucleation.

Moreover, since the concentration of free ions in this solution is very high, the crystal can be easily formed by heterogenous nucleation at low temperature or even in condition that high energy is needed such as on deficiently charged surface. As a result, a calcium phosphate crystal film can be formed on the surface of various materials even in conditions in which it has been impossible to form the crystal by the previously developed art.

In addition, the present invention provides a method for preparation of the thin film of calcium phosphate crystal comprising the steps of:

1) preparing a highly concentrated solution of calcium and phosphate ions by dissolving calcium phosphate crystals or salts of calcium and of phosphate in acidic solution (step 1);

2) mixing the acidic solution of highly concentrated calcium and phosphate ions of the step 1 with alkaline solution at low temperature (step 2);

3) excluding amorphous calcium phosphate particles or crystals which can act as nuclei for nucleation and growth of crystals, from the solution prepared in step 2, to inhibit further nucleation reaction and growth of crystals in solution (step 3); and 4) applying the solution prepared in step 3 to a solid surface to form the thin film of calcium phosphate crystal (step 4).

The thin film of calcium phosphate crystal can be prepared by contacting the said supersaturated solution of calcium and phosphate ions to a solid surface and incubating that.

The temperature of formation of thin film in step 4 is 0–60° C. Preferably 0–37° C. for initiating crystal formation on the surface and 0–60° C. for proliferation and maturation of crystals. And the period of the initiating step and the proliferation and maturation step can be varied according to the reaction condition and the surface type.

The surface for forming crystal film contains surface of materials such as metals, ceramics, organic polymers, glasses, biotissues of animals or plants, etc. For example, the said solution can be applied to porous polymers such like polyglycolic acid, polylactic acid, poly(lactic-glycolic acid) copolymer that are increasing in use for drug and cell delivery as well as giving a scaffold for bone ingrowth, for preparation of thin film of calcium phosphate apatite.

Also the geometric structure of the material is not limited. Therefore, it contains various structures such as flat plates, circular cylinders, cubes, cones, square pillars, their complex, etc. And the solid surface can be uncharged as well as charged.

The supersaturated solution of calcium and phosphate ions prepared according to the present invention can be very highly concentrated by lowering the temerature. The lowered temperature inhibits a homogeneous nucleation of calcium phosphate. And the highly concentrated solution can be further stabilized by using suitable buffer system, i.e. by selecting suitable acidic solution and suitable alkaline solution.

Particularly, the concentration of calcium phosphate supersaturated solution of the present invention is extremely high compared with that according to the previous art, and it is possible to form the thin film of calcium phosphate crystal rapidly on any surface such as metals, ceramics, organic polymers, glasses, tissues of animals or plants, etc. In addition, the thin film of crystal can be formed on surface even at low temperature of 0–60° C. by using the said solution. Furthermore, the thin film of calcium phosphate prepared by using the said solution has biocompatibility which allows various cells such as fibroblast, osteoblasts, osteoclasts, periodontal ligament cells, etc., to attach and proliferate on the surface, and has potential applicability to biomaterials.

Practically and presently preferred embodiments of the present invention are illustrative as shown in the following examples.

However, it will be appreciated that those skilled in the art, on consideration of this disclosure, may make modification and improvements within the spirit and scope of the present invention.

EXAMPLE 1

Preparation of a Supersaturated Calcium Phosphate Solution 1

A solution of 17.7 mg of $Ca(NO_2)_2 \cdot 4H_2O$ dissolved in 250 ml of distilled water and a solution of 40 mg of $(NH_4)_2HPO_4$ and 1 ml of liq. ammonia dissolved in 500 ml of distilled water were quickly mixed, filtered and freeze-dried to synthesize apatite crystal. 400 mg of apatite crystal was dissolved in 40 ml of 0.2 MHCl to prepare an acidic ion solution containing calcium phosphate ion. The acidic solution was diluted with 0.2 M HCl to make the concentration of calcium phosphate to be 15%. The solution was mixed with 0.2 N NaOH and stirred to prepare ion solution of pH 7.4. The temperature of all the above solutions was maintained at 4° C. At this time amorphous calcium phosphate was quickly formed. However there were free ions which had not taken part in formation of amorphous calcium phosphate particles owing to low temperature, and the amount of precipitated crystal was slowly reduced and equilibrated. The solution was left for 10 min at 4° C., and the amorphous calcium phosphate produced was excluded by filtering with 0.2 micrometer size filter, to prepare a neutralized ionic buffer solution.

The ion concentration product of the prepared solution was determined to be 15–20 mM² $[Ca^{2+}] \times [HPO_4^{2-}]$ by atomic absorption spectroscopy (Perkin Elmer, USA) and calorimetric method, that is, the solution was supersaturated.

The supersaturated solution prepared above was stored at 4° C. until used.

EXAMPLE 2

Preparation of a Supersaturated Calcium Phosphate Solution 2

A calcium phosphate solution was prepared by the same condition of example 1 except that the alkaline solution of 0.2 M Tris[hydroxymethyl]aminomethane in place of 0.2 N NaOH was used to prepare Tris-HCl buffer solution of pH 7.4.

The ion concentration product of the prepared solution was determined to be 15–20 mM² $[Ca^{2+}] \times [HPO_4^{2-}]$ by atomic absorption spectroscopy (Perkin Elmer, USA) and calorimetric method, that is, the solution was supersaturated.

The supersaturated solution prepared above was stored at 4° C. until used.

EXAMPLE 3

Preparation of a Supersaturated Calcium Phosphate Solution 3

A calcium phosphate solution was prepared by the same condition of example 1 except that the acidic solution was exchanged.

The acidic solution was prepared by using N-[2-hydroxyethyl]piperazine-N'-[2-ethanesulfonic acid] and HCl in place of HCl. 0.1 N HCl solution was added to 0.2 M N-[2-hydroxyethyl]piperazine-N'-[2-ethanesulfonic acid] solution whose pH was maintained at 4.0 during the process. The acidic solution containing calcium and phosphate ions was mixed with 0.2 N NaOH and stirred to prepare Hepes buffer solution of pH 7.4.

The ion concentration product of the prepared solution was determined to be 15–20 mM² $[Ca^{2-}] \times [HPO_4^{2-}]$ by atomic absorption spectroscopy (Perkin Elmer, USA) and calorimetric method, that is, the solution was supersaturated.

The supersaturated solution prepared above was stored at 4° C. until used.

EXAMPLE 4

Preparation of a Supersaturated Calcium Phosphate Solution 4

A calcium phosphate solution was prepared by the same condition of example 1 except that 93 mg of $CaCl_2 \cdot 2H_2O$ and 52 mg of $KH_2PO_4$ were dissolved directly to 75 ml of 0.2 M HCl.

The ion concentration product of the prepared solution was determined to be 15–20 mM $[Ca^{2+}] \times [HPO_4^{2-}]$ by atomic absorption spectroscopy and calorimetric method, that is, the solution was supersaturated.

The supersaturated solution prepared above was stored at 4° C. until used.

EXAMPLE 5

Preparation of a Supersaturated Calcium Phosphate Solution 5

A calcium phosphate solution was prepared by the same condition of example 4 except that the alkaline solution of 0.2 M Tris[hydroxymethyl]aminomethane in place of 0.2 N NaOH was used to prepare Tris-HCl buffer solution of pH 7.4.

The ion concentration product of the prepared solution was determined to be 15–20 mM$^2$[Ca$^{2+}$]×[HPO$_4^{2-}$] by atomic absorption spectroscopy (Perkin Elmer, USA) and calorimetric method, that is, the solution was supersaturated.

The supersaturated solution prepared above was stored at 4° C. until used.

EXAMPLE 6

Preparation of a Supersaturated Calcium Phosphate Solution 6

A calcium phosphate solution was prepared by the same condition of example 4 except that the acidic solution was exchanged.

The acidic solution was prepared by using N-[2-hydroxyethyl]piperazine-N'-[2-ethanesulfonic acid] and HCl in place of HCl. 0.1 N HCl solution was added to 0.2 M N-[2-hydroxyethyl]piperazine-N'-[2-ethanesulfonic acid] solution whose pH was maintained at 4.0 during the process. The acidic solution containing calcium and phosphate ions was mixed with 0.2 N NaOH and stirred to prepare Hepes buffer solution of pH 7.4.

The ion concentration product of the prepared solution was determined to be 15–20 mM$^2$ [Ca$^{2+}$]×[HPO$_4^{2-}$] by atomic absorption spectroscopy (Perkin Elmer, USA) and calorimetric method, that is, the solution was supersaturated.

The supersaturated solution prepared above was stored at 4° C. until used.

EXAMPLE 7

Preparation of Thin Film of Apatite 1

The supersaturated solution prepared in example 1 was poured into a culture dish (Corning, USA), and incubated at 8° C. for 2 days. Then the temperature was increased to 20° C., and the culture dish to be coated was incubated further at this temperature for 24 hours to form thin film.

The thin film of calcium phosphate apatite crystal was examined by the scanning electron microscopy (SEM) (840A, JEOL, Japan). FIG. 1 shows the SEM image (X10,000) of the surface. As known in FIG. 1, the thin film of apatite prepared according to the present invention had uniform crystal size and stable structure. Dimension of crystals on the culture dishes were 16.7±3.7 nm in length and 12.2+2.4 nm in width (n=50)

The long range order of crystals which were scraped off from the surface of culture dishes, was determined by powder x-ray diffraction (XRD) (MXP 18, Mac Science, Japan) at 100 mA and 50 kV.

As a result, there was no other phase of calcium phosphate crystal but apatite in thin film. X-ray diffraction of apatite crystals showed that they were low in crystallinity like that of bone crystals (See Table 1). Extremely small dimension of crystals can give them an extensive specific area, which would enable them to be highly interactive in cellular or organic environment with high surface reactivity.

TABLE 1

| XRD data of thin film of calcium phosphate crystal | | | | |
|---|---|---|---|---|
| 2 theta | d | I (cps) | I/I$_0$ | FWHM |
| 22.70 | 3.9139 | 714 | 255 | 0.58 |
| 25.98 | 3.4267 | 832 | 745 | 0.44 |

TABLE 1-continued

| XRD data of thin film of calcium phosphate crystal | | | | |
|---|---|---|---|---|
| 2 theta | d | I (cps) | I/I$_0$ | FWHM |
| 27.84 | 3.2019 | 686 | 251 | 0.32 |
| 31.72 | 2.8185 | 828 | 807 | 0.38 |
| 32.16 | 2.7809 | 865 | 1000 | 0.44 |
| 33.14 | 2.7009 | 627 | 218 | 0.20 |

EXAMPLE 8–12

Preparation of Thin Films of Apatite 2–6

Thin films of apatite were formed under the same condition of example 7 by using the solutions prepared in example 2, 3, 4, 5 and 6, respectively.

The SEM images of the thin films of apatite prepared were similar to that of the thin film prepared in example 7. That is, the thin films of apatite prepared had uniform crystal size and stable structure.

EXAMPLE 13

Preparation and Biocompatibility Test of Thin Film of Apatite 1

A thin film of apatite was formed under the same condition of example 7 except using polyglactin 910 (vicryl) fiber instead of a culture dish. Then the fiber on which thin film of apatite had been formed, was placed in L929 fibroblast (ATCC NCTC clone 929) culture medium and cultured in CO$_2$ incubator supplied with 95% air and 5% CO$_2$ at 37° C. After 3 days, the fiber was examined by SEM (X1,300).

Figure 2:
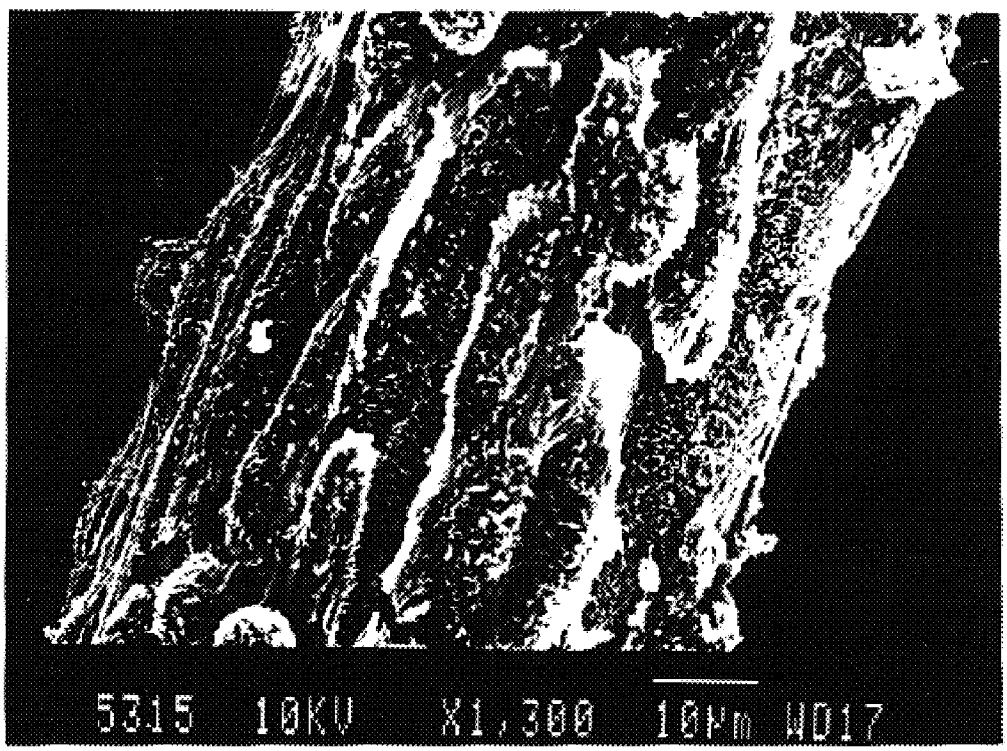
FIG. 2 is the SEM image (X1,300) of the fibroblast cultured on the thin film of apatite crystals formed on a fiber surface.

As shown in FIG. 2, cells were attached and proliferated uniformly and stably on the thin film of calcium phosphate apatite. As a result, it was confirmed that the thin film of calcium phosphate apatite prepared according to the present invention has biocompatibility.

EXAMPLE 14–18

Preparation and Biocompatibility Test of Thin Films of Apatite 2–6

Thin films of apatite were formed under the same condition of example 13 by using the solutions prepared in example 2, 3, 4, 5 and 6, respectively. Then fibroblast was cultured on the said thin films of apatite under the same condition of example 13.

The SEM images of the thin films of apatite prepared were similar to that of the thin film prepared in example 13. That is, cells were attached and proliferated uniformly and stably on the thin film of calcium phosphate apatite.

What is claimed is:

1. A method for preparation of a supersaturated solution of calcium phosphate comprising the steps of:
   1) preparing a solution of calcium and phosphate ions by dissolving calcium phosphate crystals or salts of calcium and of phosphate in acidic solution (step 1);
   2) mixing the acidic solution of calcium and phosphate ions of the step 1 with an alkaline solution at a temperature, wherein the temperature of an acidic solution and of an alkaline solution and the reaction temperature of step 2 are 0–37° C. (step 2); and
   3) excluding amorphous calcium phosphate particles or crystals which can act as nuclei for nucleation and growth of crystals, from the solution prepared in step 2, to inhabit fiber nucleation reaction and growth of crystals in solution (step 3) to produce a supersaturated solution of calcium phosphate.

2. The method for preparation of supersaturated solution of calcium phosphate according to claim 1, wherein the acidic solution of step 1 is prepared by using an inorganic acid, an organic acid or their mixture.

3. The method for preparation of supersaturated solution of calcium phosphate according to claim 2, wherein the inorganic acid is selected from the group consisting of HCl, HBr, HI, $H_2SO_4$, $H_3PO_4$, $HNO_3$ and $H_2CO_3$, and the organic acid selected from the group consisting of N-[2-hydroxymethyl]piperazine-N'-[2-ethanesulfonic acid], N-tis-[hydroxymethyl]methyl-2-aminoethanesulfonic acid, 1,4-piperazinediethanesulfonic acid, (3-N-morpholino) propanesulfonic acid and $CH_3COOH$.

4. The method for preparation of supersaturated solution of calcium phosphate according to claim 1, wherein the alkaline solution of step 2 is prepared by using an inorganic base, an organic base or their mixture.

5. The method for preparation of supersaturated solution of calcium phosphate according to claim 4, wherein the inorganic base is selected from the group consisting of NaOH, KOH, LiOH, $Ca(OH)_2$, $Mg(OH)_2$ and $NH_4OH_2$ and the organic base is selected group consisting of tris [hydroxymethyl]amino methane, bis[2-hydroxyethyl] aminotris[hydroxymethyl]methane and 1,3-bis[tris (hydroxymethyl)methylamino]propane.

6. The method for preparation of supersaturated solution of calcium phosphate according to claim 1, wherein the pH of solution in step 2 is set to be 6.0–8.0 by adding an alkaline solution.

7. The method for preparation of supersaturated solution of calcium phosphate according to claim 1, wherein amorphous calcium phosphate particles or crystals in step 3 is excluded by filtration with a porous filter or by centrifugation.

8. A method for preparation of the thin film of calcium phosphate crystal by coating the supersaturated solution of calcium phosphate to a solid surface, comprising the steps of:

1) preparing a solution of calcium and phosphate ions by dissolving calcium phosphate crystals or salts of calcium and of phosphate in acidic solution (step 1);

2) mixing the acidic solution of calcium and phosphate ions of the step 1 with alkaline solution at a temperature, wherein the temperature of the acidic solution and of the alkaline solution and the reaction temperature of step 2 are 0–37° C. (step 2);

3) excluding amorphous calcium phosphate particles or crystals can act as nuclei for nucleation and growth of crystals, which from the solution prepared in step 2, to inhibit further nucleation reaction and growth of crystals in solution (step 3) to produce a supersaturated solution of calcium phosphate; and 4) coating the supersaturated solution of calcium phosphate produced in step 3 to a solid surface at a temperature of 0–60° C.

9. The method for preparation of thin film of calcium phosphate crystal according to claim 8, including the steps of initiating (1) crystal formation and (2) proliferation and maturation of crystals, wherein the temperature for the initiating step is 0–37° C., and the temperature for the proliferation and maturation step is 0–60° C.

10. The method for preparation of thin film of calcium phosphate crystal according to claim 8, wherein the solid surface is charged or uncharged.

11. The method for preparation of thin film of calcium phosphate crystal according to claim 8, wherein the solid surface is the surface of materials selected from the group consisting of metals, ceramics, organic polymers, glasses, and biotissues of animals or plants.

* * * * *

UNITED STATES PATENT AND TRADEMARK OFFICE
CERTIFICATE OF CORRECTION

PATENT NO. : 6,720,023 B1
DATED : April 13, 2004
INVENTOR(S) : Kim et al.

It is certified that error appears in the above-identified patent and that said Letters Patent is hereby corrected as shown below:

Column 9,
Line 2, "fiber" should be corrected to read -- further --.
Line 14, "hydroxymethyl" should be corrected to read -- hydroxymethyl --.
Line 15, "N-tis" should be corrected to read -- N-tris --.
Line 25, "$NH_4OH_2$" should be corrected to read -- $NH_4OH$ --.

Column 10,
Lines 1 and 2, "the" should be corrected to read -- a --.
Line 14, -- which -- should be inserted after the word "crystals".
Line 15, after "crystals", the word "which" should be deleted.

Signed and Sealed this

Seventeenth Day of August, 2004

JON W. DUDAS
*Acting Director of the United States Patent and Trademark Office*